(12) United States Patent
Rao et al.

(10) Patent No.: US 7,915,451 B2
(45) Date of Patent: *Mar. 29, 2011

(54) CRYSTALLINE LEVOSALBUTAMOL SULPHATE AND POLYMORPHIC FORMS THEREOF

(75) Inventors: Dharmaraj Ramchandra Rao, Thane (IN); Rajendra Narayanrao Kankan, Mumbai (IN); Alka Chaudhary, Panvel (IN)

(73) Assignee: CIPLA Limited, Mumbai (IN)

( * ) Notice: Subject to any disclaimer, the term of this patent is extended or adjusted under 35 U.S.C. 154(b) by 0 days.

This patent is subject to a terminal disclaimer.

(21) Appl. No.: 12/502,608

(22) Filed: Jul. 14, 2009

(65) Prior Publication Data

US 2009/0325915 A1    Dec. 31, 2009

Related U.S. Application Data

(62) Division of application No. 11/305,226, filed on Dec. 19, 2005, now Pat. No. 7,579,505.

(30) Foreign Application Priority Data

Dec. 17, 2004   (IN) .......................... 1356/MUM/2004
Jan. 14, 2005   (IN) ............................. 40/MUM/2005

(51) Int. Cl.
*C07C 213/00* (2006.01)
(52) U.S. Cl. ...................................... 564/355; 514/686

(58) Field of Classification Search .................. None
See application file for complete search history.

(56) References Cited

U.S. PATENT DOCUMENTS

| | | | |
|---|---|---|---|
| 5,545,745 A | 8/1996 | Gao et al. | 560/42 |
| 6,585,958 B1 * | 7/2003 | Keller et al. | 424/45 |
| 6,995,286 B2 | 2/2006 | Hamied et al. | 564/365 |
| 7,005,629 B2 | 2/2006 | Flem | 250/223 B |
| 7,579,505 B2 * | 8/2009 | Rao et al. | 564/355 |
| 2002/0076382 A1 | 6/2002 | Kaplan et al. | 424/43 |

FOREIGN PATENT DOCUMENTS

WO    WO 2004/052835    6/2004

* cited by examiner

*Primary Examiner* — Sudhakar Katakam
(74) *Attorney, Agent, or Firm* — Baker & Hostetler LLP (57) ABSTRACT

The invention provides three polymorphic forms of crystalline levosalbutamol sulphate designated herein as Forms I, II and III.

Crystalline levosalbutamol sulphate Form I is characterised by a powder XRD pattern with peaks at 10.8, 11.9, 13.0, 18.3, 28.5±0.2 degrees 2 theta.

Crystalline levosalbutamol sulphate Form II is characterised by a powder XRD pattern with peaks at 8.7, 9.6, 15.2, 15.7, 19.1, 27.2, 30.7±0.2 degrees 2 theta.

Crystalline levosalbutamol sulphate Form III is characterised by a powder XRD pattern with peaks at 5.5, 6.9, 7.3, 18.7±0.2 degrees 2 theta.

Processes for making the new polymorphic forms and pharmaceutical compositions comprising them are also provided.

16 Claims, 6 Drawing Sheets

FIG 6
FORM III

CRYSTALLINE LEVOSALBUTAMOL SULPHATE AND POLYMORPHIC FORMS THEREOF

CROSS-REFERENCE TO RELATED APPLICATIONS

This application claims benefit of and is a divisional of U.S. patent application Ser. No. 11/305,226, filed Dec. 19, 2005, entitled now U.S. Pat. No. 7,579,505 "Crystalline Levosalbutamol Sulphate and Polymorphic Forms Thereof," which claims priority to Indian Patent Application Serial No. 1356/MUM/2004, filed Dec. 17, 2004, entitled "Novel Polymorphs of Pharmaceutical Active Ingredient" and Indian Patent Application Serial No. 40/MUM/2005, filed Jan. 14, 2005, entitled "Novel Polymorphs of Pharmaceutical Active Ingredient," the specifications of which are hereby incorporated by reference in their entirety.

FIELD OF THE INVENTION

The present invention relates to crystalline levosalbutamol sulphate, polymorphs thereof, processes for making the crystalline material, and compositions thereof.

BACKGROUND OF THE INVENTION

Salbutamol (albuterol) is an antihistaminic compound and is a beta 2-adrenoceptor agonist used as a bronchodilator for the treatment of asthma and as a uterine relaxant for the suspension of premature labour. Salbutamol has been marketed as a racemic mixture, although the beta 2-agonist activity resides almost exclusively in the (R)-enantiomer. The enantioselective disposition of salbutamol and the possibility that (S)-salbutamol has adverse effects have led to the development of an enantiomerically pure (R)-salbutamol formulation known as levosalbutamol (levalbuterol) (Formula I).

Formula I

A process for the preparation of optically pure salbutamol from mono protected salbutamol precursor is disclosed in U.S. Pat. No. 5,545,745.

US2004114136 and WO2004052835 describe a process for preparing levalbuterol L-tartrate in crystalline form; a pharmaceutical composition comprising levalbuterol L-tartrate, in crystalline form; a metered dose inhaler comprising a canister containing an aerosol formulation of levalbuterol L-tartrate in crystalline form; and a method of affecting bronchodilation in a patient using levalbuterol L-tartrate, including levalbuterol L-tartrate specifically in crystalline form.

Levosalbutamol is prepared by hydrogenating R-benzyl salbutamol in the presence of palladium on carbon.

R-benzyl salbutamol can be prepared by the process described in U.S. Pat. No. 5,545,745.

SUMMARY OF THE INVENTION

The object of the present invention is to provide novel and stable polymorphic forms of levosalbutamol sulphate named herewith as Form I, Form II and Form III.

Another object of the present invention is to provide processes for the preparation of these novel polymorphs of levosalbutamol sulphate.

The invention further provides processes for the inter-conversion of these forms.

There is also provided crystalline levosalbutamol sulphate (Form I) characterised by a powder XRD pattern with peaks at 10.8, 11.9, 13.0, 18.3, 28.5±0.2 degrees 2 theta.

In another aspect, there is provided crystalline levosalbutamol sulphate (Form II) characterised by a powder XRD pattern with peaks at 8.7, 9.6, 15.2, 15.7, 19.1, 27.2, 30.7±0.2 degrees 2 theta.

In a further aspect, there is also provided crystalline levosalbutamol sulphate (Form III) characterised by a powder XRD pattern with peaks at 5.5, 6.9, 7.3, 18.7±0.2 degrees 2 theta.

The invention also provides various processes for making the novel polymorphs.

In one aspect, the invention provides a process for preparing crystalline levosalbutamol sulphate Form I, which process comprises a) preparing levosalbutamol in an organic solvent b) adjusting the pH by addition of sulphuric acid at from 1 to 10° C. c) isolating the product (Form I) at from 0 to 10° C.

There is also provided a process for preparing crystalline levosalbutamol sulphate Form I, which process comprises a) dissolving any form of levosalbutamol sulphate in water b) combining the solution from step a) with a water miscible organic solvent so as to cause precipitation c) isolating Form I thereon.

The invention also provides a process for preparing crystalline levosalbutamol sulphate Form II, which process comprises a) dissolving any form of levosalbutamol sulphate in water b) distilling to residue c) stripping the residue with an organic solvent d) slurrying the solid in an organic solvent e) isolating crystalline Form II.

A further process for preparing Form II comprises jet milling any other form of levosalbutamol sulphate, for example jet milling crystalline Form I.

In another aspect, there is provided a process for preparing crystalline levosalbutamol sulphate Form III, which process comprises a) preparing levosalbutamol in an organic solvent b) adjusting the pH by addition of sulphuric acid at 25 to 30° C. c) isolating the product (Form III) at 25 to 30° C.

In a further aspect, the invention provides a process for preparing Form III which process comprises a) dissolving any form of levosalbutamol sulphate in water b) combining the solution from step a) with a water-miscible organic solvent so as to cause precipitation c) isolating Form III therefrom at ambient temperature (25 to 30° C.).

The invention also provides a pharmaceutical composition comprising a compound of the invention and a pharmaceutically acceptable carrier.

The novel compounds, and compositions thereof, are also provided for use as medicaments, particularly in the treatment of respiratory disorders and related conditions.

BRIEF DESCRIPTION OF THE DRAWINGS

Table 1 gives the numerical XRD data for FIG. 1 (Form I).
Table 2 gives the numerical XRD data for FIG. 3 (Form II).
Table 3 gives the numerical XRD data for FIG. 5 (Form III).

DETAILED DESCRIPTION

The present invention provides a novel crystalline form of levosalbutamol sulphate which is designated as Form I. Levosalbutamol sulphate crystalline Form I is characterized by an X-ray powder diffraction pattern having significant reflections expressed as 2 theta values at about 10.781, 11.941, 13.002, 18.341, 28.541±0.2 degrees, as will be clear from Table 1.

Figure 1:
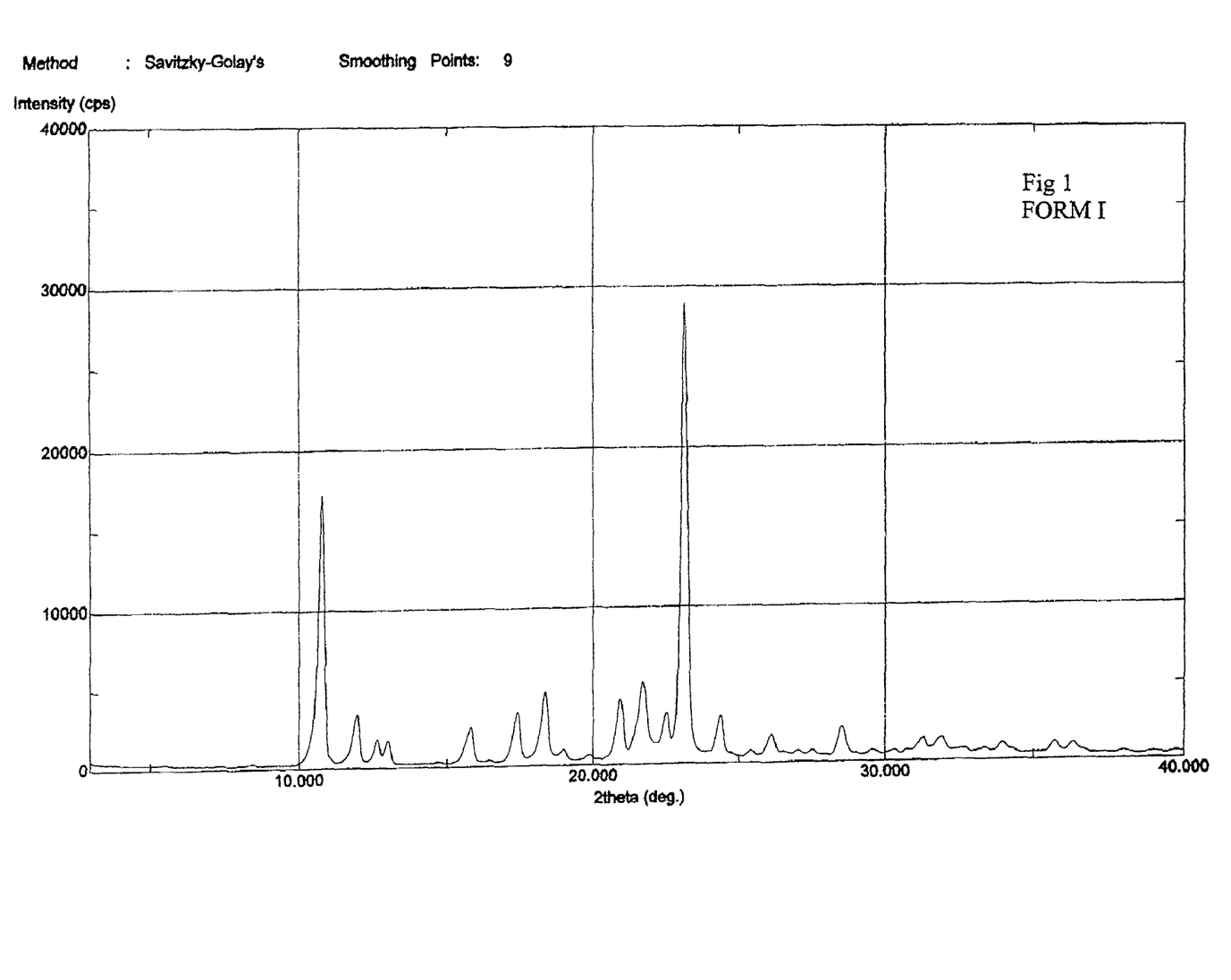
FIG. 1 shows the X-ray powder diffraction pattern of levosalbutamol sulphate Form I.

The X-ray powder diffractogram of levosalbutamol sulphate crystalline Form I is shown in FIG. 1. The major peaks and their intensities of X-ray powder diffractogram are shown in Table 1. The intensities of the reflections are also expressed as percent of most intense reflection.

Other preferred significant reflections for Form I expressed as 2 theta values include 12.66, 15.819, 17.4, 20.939, 21.72, 22.5, 23.14, 24.341, 26.12, 31.28, 31.93±0.2 degrees. The X-ray powder diffractograms for all the polymorphic Forms disclosed herein were collected on Rigaku d-max 2200 model X-ray diffractometer using Cu K α radiation (λ=1.5405 A°).

Levosalbutamol sulphate crystalline Form I is also characterised by an IR spectrum with peaks at 3568, 3307, 2980, 2799, 2561, 2458, 1615, 1508, 1440, 1380, 1342, 1258, 1200, 1112, 1082, 1029, 976, 915, 836, 793, 775, 752, 648, 617, 535, 497, 453 cm$^{-1}$.

Figure 2:
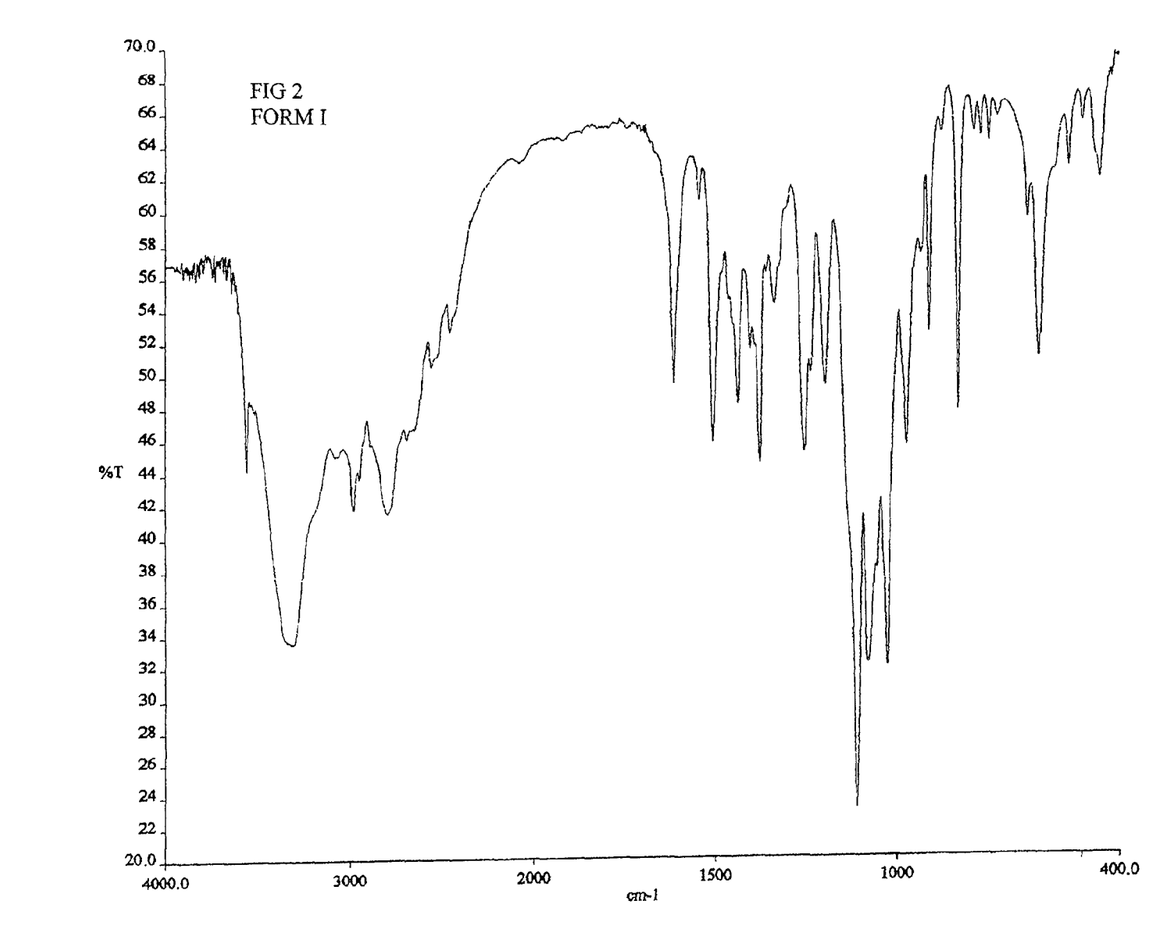
FIG. 2 shows an IR spectrum of levosalbutamol sulphate Form I.

FIG. 2 shows the IR spectrum for Form I. The IR spectra for all the polymorphic Forms disclosed herein were collected using the Spectrum-1 make of Perkin Elmer Sample and analysed as KBr pellets in the region of 4000-400 cm$^{-1}$.

In the preparation of levosalbutamol sulphate crystalline Form I, preferably R-benzyl salbutamol is hydrogenated using a catalyst, preferably a palladium on carbon catalyst, in a large volume of a suitable organic solvent. Preferably an alcoholic solvent is used, more preferably ethyl alcohol. Suitably the process is performed under hydrogen pressure, preferably at 30 psi. The catalyst is preferably then filtered and the pH of the filtrate is adjusted, preferably to 5-5.5 and preferably at 0-10° C. with sulfuric acid, suitably concentrated sulphuric acid, to provide crystals, which are filtered and dried to afford levosalbutamol sulphate Form I. The product (Form I) may be obtained by isolating at 0-10° C.

The present invention also provides another novel crystalline form of levosalbutamol sulphate, which is designated as Form II. Levosalbutamol sulphate crystalline Form II is characterized by an X-ray powder diffraction pattern having significant reflections expressed as 2 theta values at about 8.701, 9.636, 15.180, 15.657, 19.139, 27.199, 30.702±0.2 degrees, as will be clear from Table 2.

Figure 3:
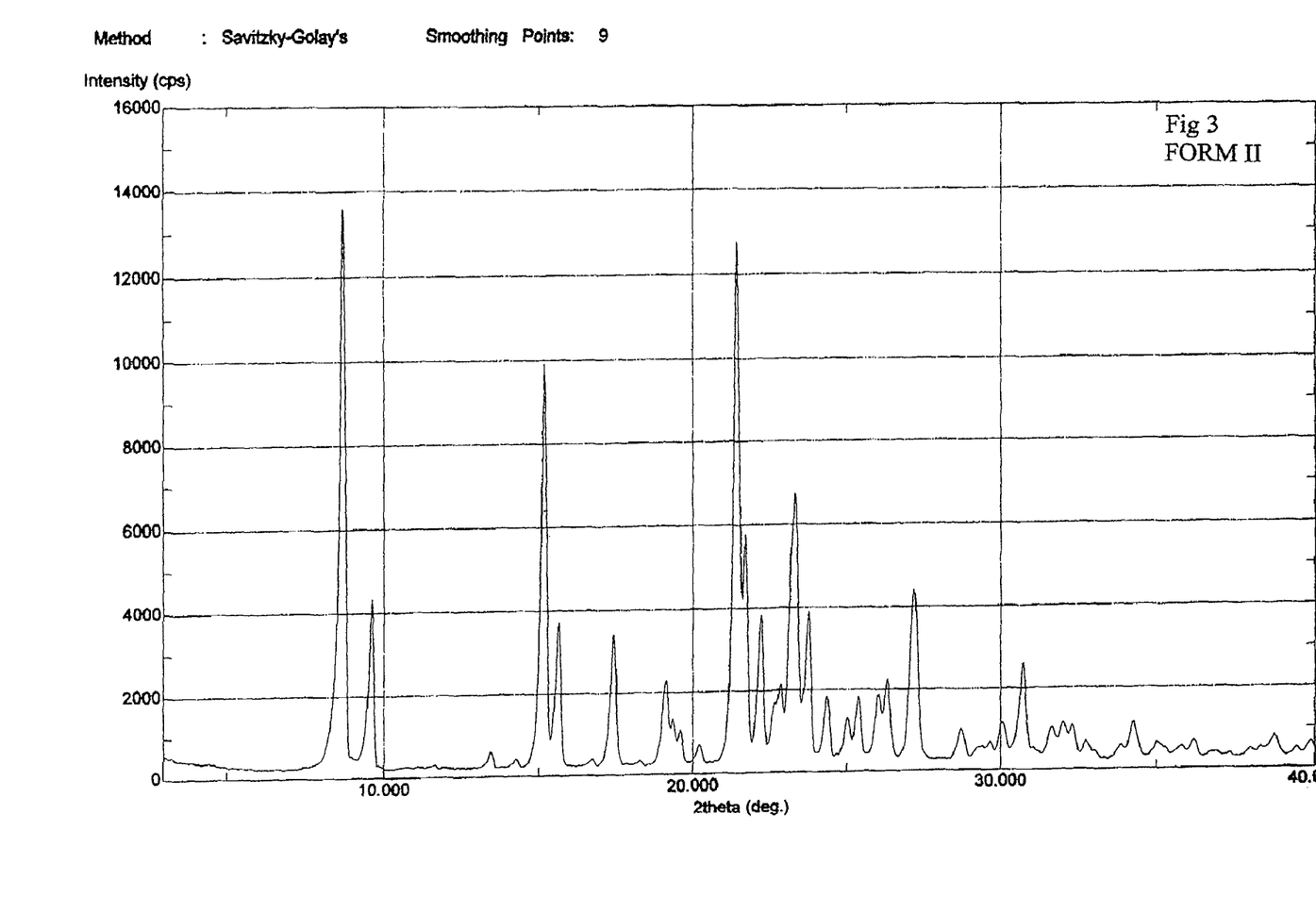
FIG. 3 shows the X-ray powder diffraction pattern of levosalbutamol sulphate Form II.

The X-ray powder diffractogram of levosalbutamol sulphate Form II is shown in FIG. 3. The major peaks and their intensities of X-ray powder diffractogram are shown in Table 2. The intensities of the peaks are expressed as percent of most intense reflection.

Other preferred significant reflections for Form II expressed as 2 theta values include peaks at about 8.701, 9.636, 15.180, 18.657, 17.44, 19.139, 21.699, 22.201, 22.837, 23.339, 23.76, 24.361, 25.022, 25.399, 26.059, 26.321, 27.199, 30.702±0.2 degrees.

Levosalbutamol sulphate crystalline Form II is also characterised by an IR spectrum with peaks at 3393, 3026, 2982, 2822, 2463, 1630, 1614, 1513, 1484, 1448, 1380, 1321, 1279, 1258, 1235, 1204, 1155, 1093, 1066, 1036, 1023, 919, 900, 838, 829, 818, 808, 788, 618, 596, 540, 493, 453, 440 cm$^{-1}$.

Figure 4:
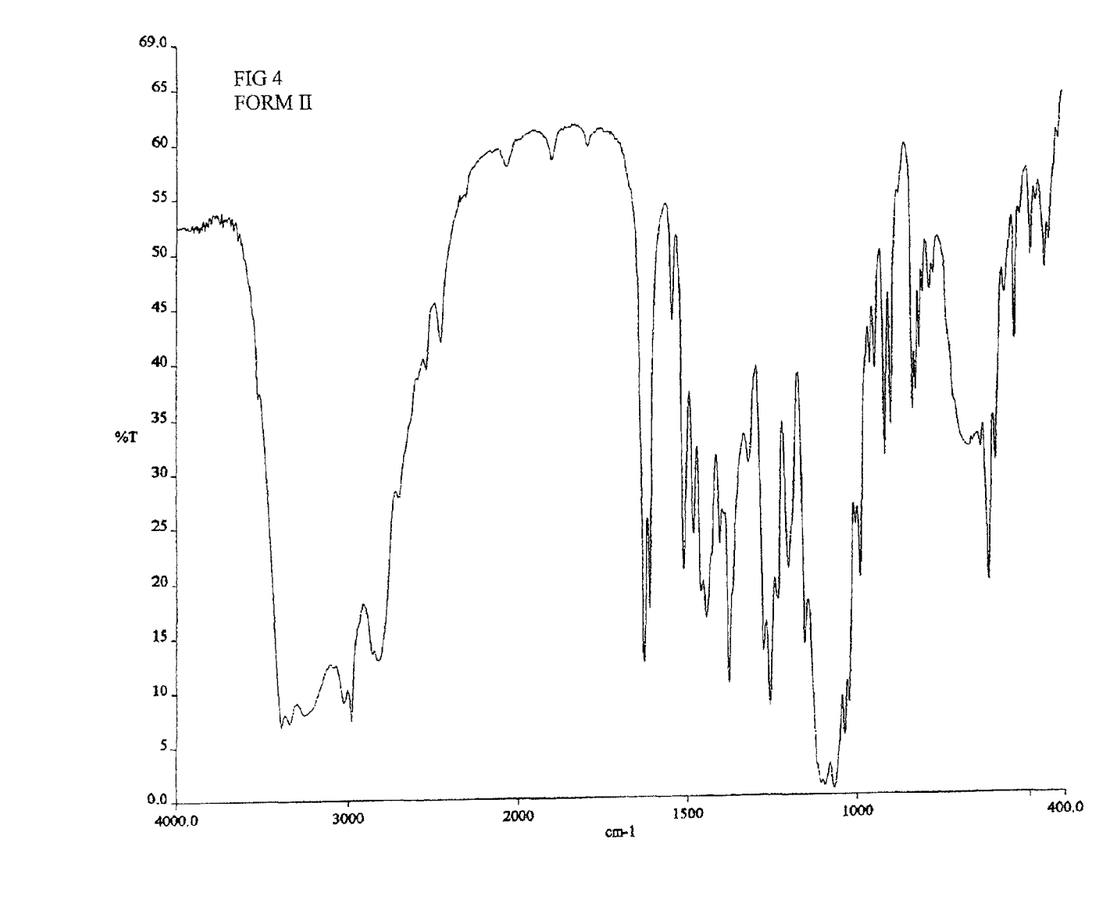
FIG. 4 shows an IR spectrum of levosalbutamol sulphate Form II.

FIG. 4 shows the IR spectrum for Form II.

A further aspect of the present invention provides a process for the preparation of levosalbutamol sulphate crystalline Form II. The process comprises dissolving any form of levosalbutamol sulphate in water and distilling it to residue. The residue is further stripped with an organic solvent, which is preferably water miscible and is preferably acetone, and the solid further slurried in a solvent, preferably the same solvent, and isolating the solid, preferably by filtering the solid and drying under vacuum to give levosalbutamol sulphate Form II.

The present invention also provides another novel crystalline form of levosalbutamol sulphate, which is designated as Form III. Levosalbutamol sulphate crystalline Form III is characterized by an X-ray powder diffraction pattern having significant reflections expressed as 2 theta values at about 5.496, 6.901, 7.340, 18.660±0.2 degrees, as will be clear from Table 3.

Figure 5:
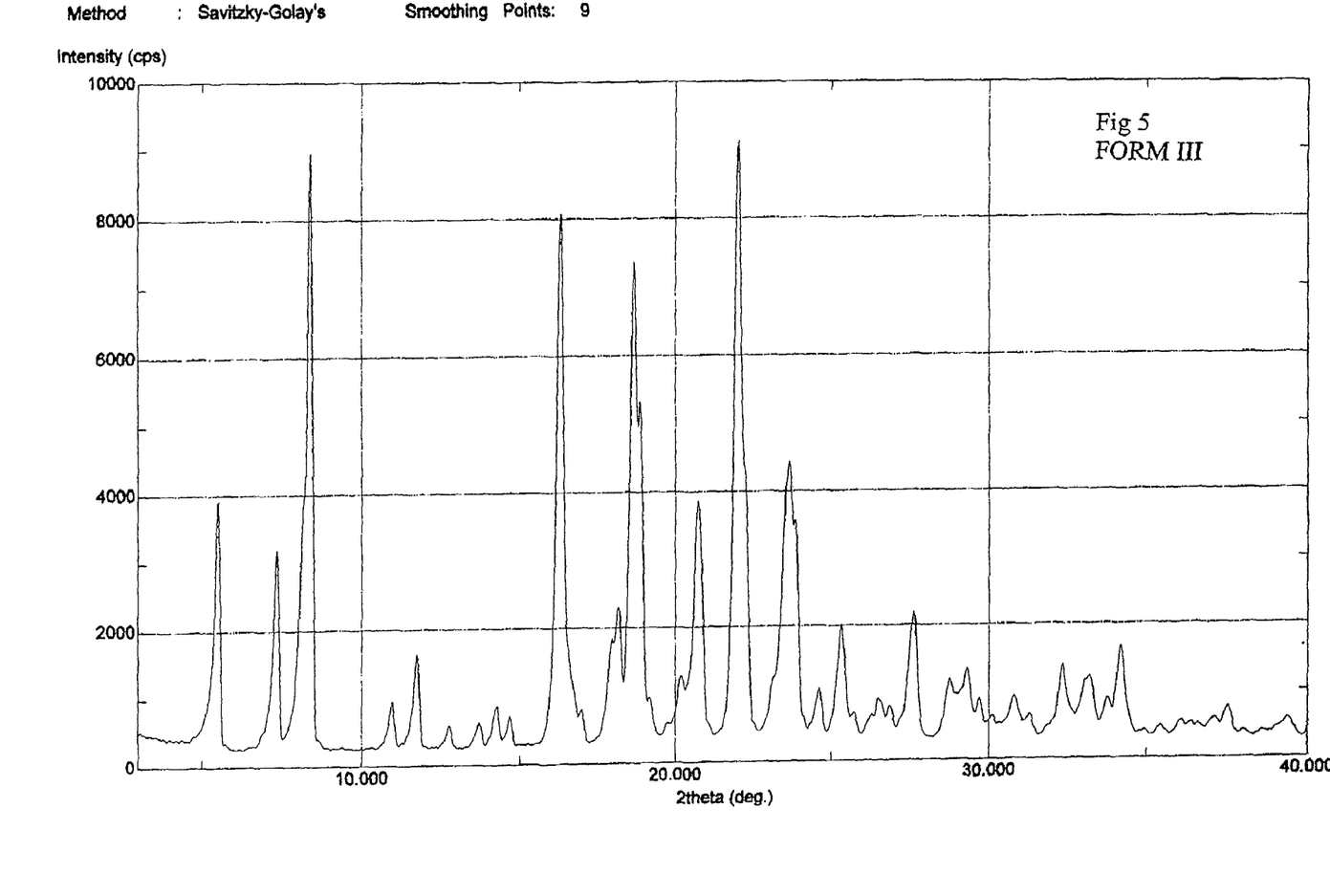
FIG. 5 shows the X-ray powder diffraction pattern of levosalbutamol sulphate Form III.

The X-ray powder diffractogram of levosalbutamol sulphate Form III is shown in FIG. 5. The major peaks and their intensities of X-ray powder diffractogram are shown in Table 3. The intensities of the peaks are also expressed as a percent of the most intense reflection.

Other preferred significant reflections for Form III expressed as 2 theta values include peaks at about 5.496, 6.901, 7.340, 8.18, 8.399, 10.978, 11.758, 14.298, 16.321, 17.98, 18.18, 18.660, 18.86, 19.189, 20.179, 20.72, 20.019, 22.219, 23.121, 23.64, 23.858, 24.638, 25.339, 27.62, 28.79, 29.319, 30.80, 32.341, 33.218, 33.781, 34.181±0.2 degrees.

Levosalbutamol sulphate crystalline Form III is also characterised by an IR spectrum with peaks at 3533, 3412, 3086, 2979, 2823, 2799, 1613, 1547, 1505, 1437, 1397, 1380, 1365, 1353, 1303, 1256, 1243, 1198, 1110, 1133, 1086, 1075, 1055, 1029, 990, 949, 919, 838, 792, 737, 723, 640, 618, 563, 536, 480, 442, 425 cm$^{-1}$.

Figure 6:
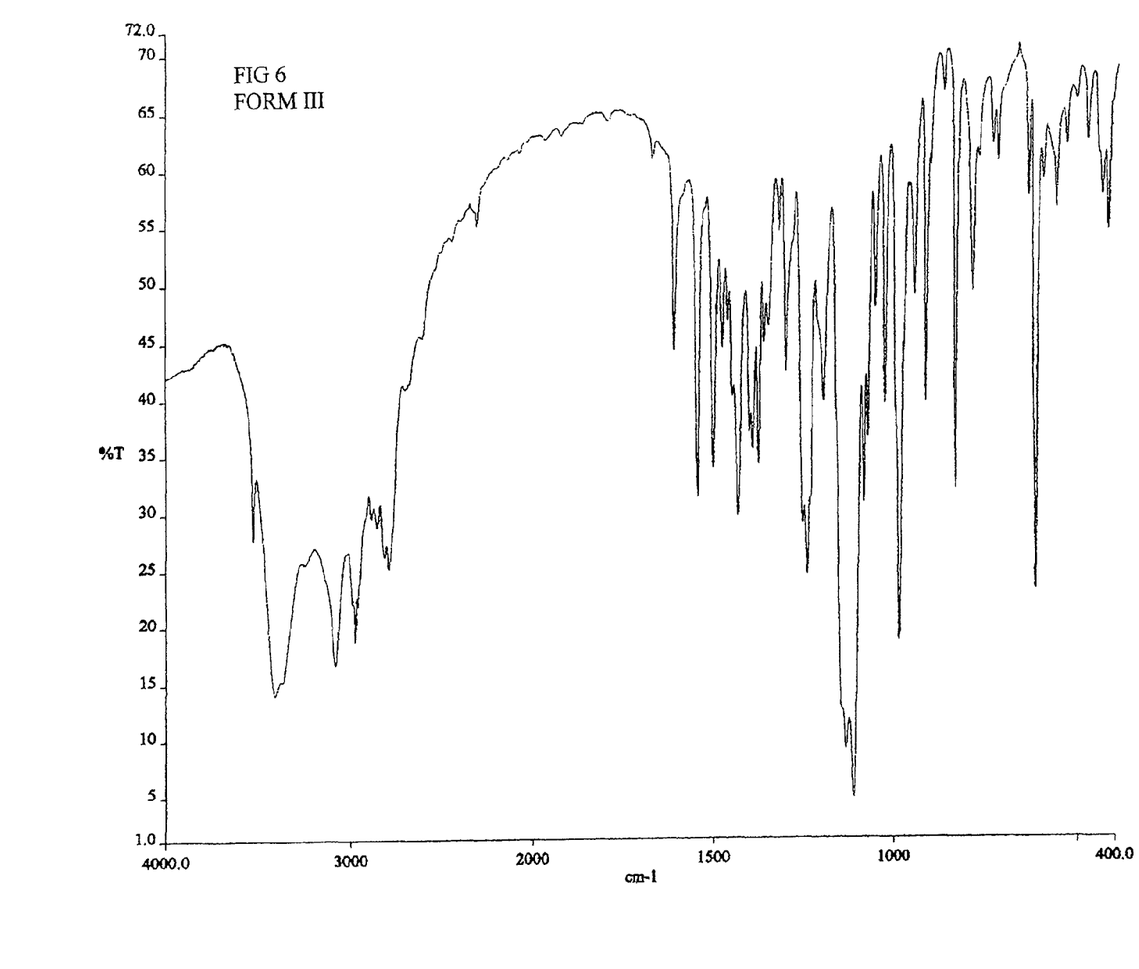
FIG. 6 shows an IR spectrum of levosalbutamol sulphate Form III.

FIG. 6 shows the IR spectrum for Form III.

A further aspect of the present invention provides a process for the preparation of levosalbutamol sulphate crystalline Form III. Preferably R-benzyl salbutamol is hydrogenated using a catalyst, preferably a palladium on carbon catalyst in a suitable organic solvent, preferably an alcoholic solvent, more preferably ethyl alcohol. Preferably this is done under hydrogen pressure, preferably at about 30 psi. Form III can be isolated by adjusting the pH by addition of sulphuric acid at ambient temperature (25 to 30° C.) and isolating the product at ambient temperature (25 to 30° C.). Preferably, these steps are done by filtering the catalyst and washing, for example with denatured alcohol. The pH of the filtrate is preferably adjusted to 5-5.5 at ambient temperature (25 to 30° C.) with sulfuric acid, preferably in concentrated form, to give crystals, which are filtered and dried to afford levosalbutamol sulphate Form III. The product (Form III) may be obtained by isolating at 25 to 30° C.

A further aspect of the present invention provides a process for the preparation of levosalbutamol sulphate crystalline Form II by jet milling levosalbutamol sulphate. For example, crystalline levosalbutamol Form I may be jet milled so as to give Form II.

It will be understood that crystalline levosalbutamol sulphate and the polymorphic Forms thereof disclosed herein may be formulated with conventional excipients, auxiliaries and carriers into a wide variety of pharmaceutical compositions, including but not limited to tablets, capsules, pellets, caplets, MDI, DPI, and Respule formulations, and oral liquids such as syrups. Where appropriate plain or sustained release formulations may be provided. Those skilled in the art of pharmaceutical formulation will be aware of the conventional ingredients which may be employed to formulate the above compositions. Such formulations may be made in accordance with conventional manufacturing procedures.

In particular, the compounds of the present invention may be combined with one or more other pharmaceutically active compounds, as will be clear to those skilled in the art. Any suitable combination of active materials is envisaged, provided the combination is acceptable from a pharmaceutical and regulatory standpoint. The compounds of the invention may, for example be combined with corticosteroids such as fluticasone, beclomethasone or budesonide; anticholinergic agents such as ipratropium, tiotropium or atropine; mucolytic agents such as ambroxol; xanthine derivatives such as theophylline; antihistamines; analgesics, and bronchodilators. As will be clear, the additional active or actives may be provided in any suitable form, including the pharmaceutically acceptable derivatives thereof, including salts, esters, polymorphs, and the optically active forms as well as the racemates.

The invention thus provides a pharmaceutical composition comprising crystalline levosalbutamol sulphate, particularly Form I or Form II or Form III thereof, in combination with one or more pharmaceutically active compounds and, optionally, a pharmaceutically acceptable carrier.

The following specific examples illustrate the best mode of carrying out the process of the present invention. The invention is not limited to the particular embodiments illustrated herein but includes permutations, which are obvious as set forth in the description.

EXAMPLES

Example 1

R-benzyl salbutamol (20.0 kg.), methanol (61.0 ltr.), denatured alcohol (72 ltrs.) was charged in an autoclave, palladium (5%) on charcoal (1.30 kg) was charged and stirred under 30 psi hydrogen pressure. After completion of reaction the catalyst was filtered and washed with methanol (60 lts.) and denatured alcohol (60 ltrs.). The pH of the clear filtrate was adjusted with sulphuric acid to 5-5.5 pH at 0-10° C. and the resulting solid was stirred at 0-10° C. for 1 hr., filtered and washed with methanol (20 ltrs.). The product was dried under vacuum at 30° C. for 1 hr. and further at 50-60° C. for additional 1 hr. to give R-salbutamol Form I (19.0 kg.).

Example 2

R-benzyl salbutamol (10.0 kg.), methanol (30.0 ltr.), denatured alcohol (36 ltrs.) was charged in an autoclave, wet palladium (5%) on charcoal (0.65 kg) was charged and stirred under 30 psi hydrogen pressure. After completion of reaction the catalyst was filtered and washed with denatured alcohol (25 ltrs.). The pH of the clear filtrate was adjusted with sulphuric acid to 5-5.5 pH at ambient temperature (25 to 30° C.) and the resulting solid was filtered and washed with methanol (10 ltrs.) at 25 to 30° C. The product was dried under vacuum at 50-60° C. temp to give R-salbutamol sulphate Form III (19.0 kg.).

Example 3

R-salbutamol sulphate (14.80 Kg) was dissolved in water (60.0 ltrs.) and filtered to get a clear solution. The filtrate was distilled under vacuum below 60° C. to residue. The residue was stripped with acetone (74.0 ltrs.) twice, further acetone (148.0 lts.) was added and the resulting slurry was stirred for 2 hrs. The slurry was filtered and dried under vacuum at 60° C. for 10-12 hrs to give R-salbutamol sulphate Form II (11.1 kg.)

Example 4

R-salbutamol sulphate (10 Kg) was dissolved in water (30.0 ltrs.) and stirred for 10-15 min. The resulting clear solution was filtered. Methanol (150 ltrs.) was added slowly to the clear filtrate at room temperature and stirred for 30 mins. and further chilled to 0-5° C. The resulting solid was filtered and washed with methanol. The product was dried under vacuum at 60° C. for 3-4 hrs to give R-salbutamol sulphate Form I (8 kg.)

Example 5

R-salbutamol sulphate (20 Kg) was dissolved in water (60.0 ltrs.) and filtered to get a clear solution charge 300 ltr acetone slowly at 25-30° C. and the resulting mixture was stirred for 2 hrs at room temp. The resulting slurry was filtered and dried under vacuum at 80° C. for 10-12 hrs to give R-salbutamol sulphate Form III (17 kg.)

Example 6

R-salbutamol sulphate (10 gms) was dissolved in water (30 ml). Methanol (150 ml) was charged at 25-30° C. and Isopropyl alcohol (75 ml) was added and the mixture was cooled to 5-10° C. for 2 hrs. filtered and dried at 80° C. under vacuum for 15-20 hrs. to give Form II.

Example 7

R-salbutamol sulphate was dissolved in methanol at reflux temperature. The reaction mass was then cooled to room temperature and further chilled to 5-10° C. The resulting solid was filtered and dried at 80° C. to give R-salbutamol sulphate Form II Example 8

R-salbutamol sulphate Form I was subjected to jet milling to get R-salbutamol sulphate Form II having a particle size of 90% less than 5 micron and 100% below 12.5 micron.

Note that in Examples 3 to 7 any form of R-salbutamol sulphate may be used as the stating material.

TABLE 1

LEVOSALBUTAMOL S04 - Form I

| Peak No. | 2θ (deg) | d (A) | Height | Height % | FWHM |
|---|---|---|---|---|---|
| 1 | 10.781 | 8.1998 | 10389 | 59.5 | 0.237 |
| 2 | 11.941 | 7.4053 | 2043 | 11.7 | 0.237 |
| 3 | 12.660 | 6.9865 | 1090 | 6.2 | 0.232 |
| 4 | 13.005 | 6.8036 | 1080 | 6.2 | 0.167 |
| 5 | 15.819 | 5.5975 | 1576 | 9.0 | 0.266 |
| 6 | 17.400 | 5.0924 | 2170 | 12.4 | 0.236 |
| 7 | 18.341 | 4.8332 | 2847 | 16.3 | 0.268 |
| 8 | 19.019 | 4.6624 | 621 | 3.6 | 0.271 |
| 9 | 20.939 | 4.2390 | 2564 | 14.7 | 0.265 |
| 10 | 21.720 | 4.0883 | 3195 | 18.3 | 0.282 |
| 11 | 22.500 | 3.9482 | 2001 | 11.5 | 0.202 |
| 12 | 23.140 | 3.8406 | 17446 | 100.0 | 0.234 |
| 13 | 24.341 | 3.6537 | 1870 | 10.7 | 0.243 |
| 14 | 26.120 | 3.4087 | 1108 | 6.4 | 0.285 |
| 15 | 28.541 | 3.1249 | 1379 | 7.9 | 0.281 |
| 16 | 31.280 | 2.8572 | 914 | 5.2 | 0.378 |
| 17 | 31.939 | 2.7997 | 955 | 5.5 | 0.451 |
| 18 | 33.980 | 2.6361 | 686 | 3.9 | 0.361 |
| 19 | 34.279 | 2.6138 | 419 | 2.4 | 0.350 |
| 20 | 35.739 | 2.51036 | 712 | 4.1 | 0.329 |
| 21 | 36.340 | 2.4702 | 635 | 3.6 | 0.391 |

TABLE 2

LEVOSALBUTAMOL S04 - Form II

| Peak No. | 2θ (deg) | d (A) | Height | Height % | FWHM |
|---|---|---|---|---|---|
| 1 | 8.701 | 10.1542 | 8249 | 100.0 | 0.205 |
| 2 | 9.636 | 9.1706 | 2610 | 31.6 | 0.195 |
| 3 | 13.422 | 6.5914 | 365 | 4.4 | 0.184 |
| 4 | 15.180 | 5.8318 | 6090 | 73.8 | 0.213 |
| 5 | 15.657 | 5.6550 | 2247 | 27.2 | 0.201 |
| 6 | 17.440 | 5.0809 | 2091 | 25.3 | 0.193 |
| 7 | 19.139 | 4.6335 | 1416 | 17.2 | 0.272 |
| 8 | 19.360 | 4.5811 | 900 | 10.9 | 0.385 |
| 9 | 19.583 | 4.5294 | 666 | 8.1 | 0.376 |
| 10 | 20.221 | 4.3879 | 462 | 5.6 | 0.156 |
| 11 | 21.439 | 4.1413 | 7819 | 94.8 | 0.256 |
| 12 | 21.699 | 4.0921 | 3525 | 42.7 | 0.356 |
| 13 | 22.201 | 4.0008 | 2317 | 28.1 | 0.128 |
| 14 | 22.837 | 3.8907 | 1299 | 15.7 | 0.091 |
| 15 | 23.339 | 3.8083 | 4096 | 49.7 | 0.308 |
| 16 | 23.760 | 3.7417 | 2345 | 28.4 | 0.236 |
| 17 | 24.361 | 3.6508 | 1107 | 13.4 | 0.165 |
| 18 | 25.022 | 3.5558 | 829 | 10.0 | 0.080 |
| 19 | 25.399 | 3.5038 | 1127 | 13.7 | 0.176 |
| 20 | 26.059 | 3.4166 | 1162 | 14.1 | 0.271 |
| 21 | 26.321 | 3.3832 | 1437 | 17.4 | 0.256 |
| 22 | 27.199 | 3.2759 | 2718 | 32.9 | 0.255 |
| 23 | 28.740 | 3.1037 | 622 | 7.5 | 0.193 |
| 24 | 29.263 | 3.0493 | 356 | 4.3 | 0.628 |
| 25 | 30.077 | 2.9687 | 721 | 8.7 | 0.162 |
| 26 | 30.702 | 2.9097 | 1586 | 19.2 | 0.211 |
| 27 | 31.640 | 2.8255 | 631 | 7.6 | 0.351 |
| 28 | 32.001 | 2.7944 | 700 | 8.5 | 0.464 |
| 29 | 32.319 | 2.7677 | 680 | 8.2 | 0.354 |
| 30 | 33.859 | 2.6452 | 368 | 4.5 | 0.382 |
| 31 | 34.242 | 2.6165 | 730 | 8.8 | 0.315 |
| 32 | 35.002 | 2.5615 | 424 | 5.1 | 0.244 |
| 33 | 35.299 | 2.5406 | 316 | 3.8 | 0.542 |
| 34 | 35.838 | 2.5036 | 376 | 4.6 | 0.239 |
| 35 | 36.238 | 2.4769 | 427 | 5.2 | 0.232 |
| 36 | 36.737 | 2.443 | 254 | 3.1 | 0.313 |
| 37 | 37.999 | 2.3660 | 297 | 3.6 | 0.245 |
| 38 | 38.265 | 2.3502 | 319 | 3.9 | 0.658 |
| 39 | 38.777 | 2.3203 | 491 | 6.0 | 0.380 |

TABLE 3

LEVOSALBUTAMOL S04 - Form III

| Peak No. | 2θ (deg) | d (A) | Height | Height % | FWHM |
|---|---|---|---|---|---|
| 1 | 5.496 | 16.0657 | 2337 | 41.8 | 0.206 |
| 2 | 6.901 | 12.799 | 320 | 5.7 | 0.295 |
| 3 | 7.340 | 12.034 | 1938 | 34.6 | 0.217 |
| 4 | 8.181 | 10.7983 | 2348 | 42.0 | 0.645 |
| 5 | 8.399 | 10.5187 | 5559 | 99.4 | 0.251 |
| 6 | 10.978 | 8.0527 | 577 | 10.3 | 0.190 |
| 7 | 11.758 | 7.5203 | 978 | 17.5 | 0.178 |
| 8 | 12.778 | 6.9221 | 365 | 6.5 | 0.186 |
| 9 | 14.298 | 6.1895 | 565 | 10.1 | 0.233 |
| 10 | 14.701 | 6.0206 | 428 | 7.7 | 0.165 |
| 11 | 16.321 | 5.4266 | 4839 | 86.5 | 0.292 |
| 12 | 16.981 | 5.2172 | 498 | 8.9 | 0.134 |
| 13 | 17.980 | 4.9293 | 1110 | 19.8 | 0.319 |
| 14 | 18.180 | 4.8758 | 1421 | 25.4 | 0.532 |
| 15 | 18.660 | 4.7512 | 4455 | 79.6 | 0.432 |
| 16 | 18.860 | 4.7013 | 3247 | 58.0 | 0.243 |
| 17 | 19.189 | 4.6215 | 636 | 11.4 | 0.100 |
| 18 | 20.179 | 4.3969 | 797 | 14.2 | 0.529 |
| 19 | 20.720 | 4.2833 | 2355 | 42.1 | 0.315 |
| 20 | 22.019 | 4.0335 | 5594 | 100.0 | 0.306 |
| 21 | 22.219 | 3.9976 | 2598 | 46.4 | 0.595 |
| 22 | 23.121 | 3.8436 | 761 | 13.6 | 0.563 |
| 23 | 23.640 | 3.7604 | 2729 | 48.8 | 0.460 |
| 24 | 23.858 | 3.7265 | 2189 | 39.1 | 0.547 |
| 25 | 24.638 | 3.6103 | 654 | 11.7 | 0.168 |
| 26 | 25.339 | 3.5120 | 1235 | 22.1 | 0.276 |
| 27 | 25.721 | 3.4607 | 445 | 8.0 | 0.215 |
| 28 | 26.299 | 3.3859 | 414 | 7.4 | 0.352 |
| 29 | 26.518 | 3.3585 | 550 | 9.8 | 0.354 |
| 30 | 26.879 | 3.3142 | 493 | 8.8 | 0.249 |
| 31 | 27.620 | 3.2270 | 1316 | 23.5 | 0.274 |
| 32 | 28.799 | 3.0974 | 719 | 12.9 | 0.655 |
| 33 | 29.319 | 3.0437 | 827 | 14.8 | 0.654 |
| 34 | 30.800 | 2.9006 | 565 | 10.1 | 0.319 |
| 35 | 31.242 | 2.8606 | 430 | 7.7 | 0.207 |
| 36 | 32.341 | 2.7659 | 867 | 15.5 | 0.232 |
| 37 | 33.218 | 2.6948 | 719 | 12.9 | 0.313 |
| 38 | 33.781 | 2.6512 | 565 | 10.1 | 0.245 |
| 39 | 34.181 | 2.6211 | 1029 | 18.4 | 0.267 |
| 40 | 36.646 | 2.4502 | 325 | 5.8 | 0.557 |
| 41 | 37.140 | 2.4187 | 376 | 6.7 | 0.252 |
| 42 | 37.522 | 2.3950 | 478 | 8.5 | 0.306 |
| 43 | 39.397 | 2.2852 | 356 | 6.4 | 0.427 |

The invention claimed is:

1. A process for preparing crystalline levosalbutamol sulphate (Form I) characterized by a powder X-ray diffraction (XRD) pattern with peaks at 10.8, 11.9, 13.0, 18.3, 28.5+/−0.2 degrees 2 theta, the process comprising:
   a) preparing levosalbutamol in an organic solvent, wherein the organic solvent comprises denatured alcohol or methanol or a mixture of the two;
   b) adjusting the pH by addition of sulfuric acid at from 0° C. to 10° C.; and
   c) isolating the product (Form I) at from 0° C. to 10° C.

2. The process according to claim 1 wherein in step b) the pH is adjusted to from 5 to 5.5.

3. A process for preparing crystalline levosalbutamol sulphate (Form II) characterized by a powder X-ray diffraction (XRD) pattern with peaks at 8.7, 9.6, 15.2, 15.7, 19.1, 27.2, 30.7+/−0.2 degrees 2 theta, the process comprising:
   a) dissolving any form of levosalbutamol sulphate in water;
   b) distilling to residue;
   c) stripping the residue with acetone;
   d) slurrying the solid in acetone; and
   e) isolating crystalline Form II.

4. The process according to claim 3 wherein step a) comprises dissolving crystalline levosalbutamol sulphate Form I or Form III in water.

5. A process for preparing crystalline levosalbutamol sulphate (Form III) characterized by a powder X-ray diffraction (XRD) pattern with peaks at 5.5, 6.9, 7.3, 18.7+/−0.2 degrees 2 theta, the process comprising:
   a) preparing levosalbutamol in an organic solvent, wherein the organic solvent comprises denatured alcohol or methanol or a mixture of the two;
   b) adjusting the pH by addition of sulphuric acid at 25° C. to 30° C.; and
   c) isolating the product (Form III) at 25° C. to 30° C.

6. The process according to claim 5 wherein in step b) the pH is adjusted to from 5 to 5.5.

7. A process for preparing crystalline levosalbutamol sulphate (Form I) characterized by a powder X-ray diffraction (XRD) pattern with peaks at 10.8, 11.9, 13.0, 18.3, 28.5+/−0.2 degrees 2 theta, the process comprising:
   a) dissolving any form of levosalbutamol sulphate in water;
   b) combining the solution from step a) with methanol so as to cause precipitation; and
   c) isolating Form I thereon.

8. The process according to claim 7 wherein prior to step c) the solution is cooled to from 0° C. to 5° C.

9. A process for preparing crystalline levosalbutamol sulphate (Form III) characterized by a powder X-ray diffraction (XRD) pattern with peaks at 5.5, 6.9, 7.3, 18.7+/−0.2 degrees 2 theta, the process comprising:
   a) dissolving any form of levosalbutamol sulphate in water;
   b) combining the solution from step a) with acetone so as to cause precipitation; and
   c) isolating Form III therefrom at ambient temperature.

10. The process according to claim 9 wherein the process is carried out at from 25° C. to 30° C.

11. A pharmaceutical composition comprising a crystalline levosalbutamol sulphate (Form I) characterized by a powder X-ray diffraction (XRD) pattern with peaks at 10.8, 11.9, 13.0, 18.3, 28.5+/−0.2 degrees 2 theta and a pharmaceutically acceptable carrier.

12. A pharmaceutical composition comprising a crystalline levosalbutamol sulphate (Form I) characterized by a powder X-ray diffraction (XRD) pattern with peaks at 10.8, 11.9, 13.0, 18.3, 28.5+/−0.2 degrees 2 theta in combination with one or more pharmaceutically active compounds and, optionally, a pharmaceutically acceptable carrier.

13. The pharmaceutical composition according to claim 12 wherein the further active compound is one or more of fluticasone propionate, beclomethasone dipropionate, budesonide, ipratropium bromide, ambroxol, and theophylline.

14. A compound comprising a crystalline levosalbutamol sulphate (Form I) characterized by a powder X-ray diffraction (XRD) pattern with peaks at 10.8, 11.9, 13.0, 18.3, 28.5+/−0.2 degrees 2 theta for use as a medicament.

15. The compound according to claim 14 for use in the treatment of respiratory disorders and related conditions.

16. A compound comprising a crystalline levosalbutamol sulphate (Form I) characterized by a powder X-ray diffraction (XRD) pattern with peaks at 10.8, 11.9, 13.0, 18.3, 28.5+/−0.2 degrees 2 theta and one or more pharmaceutically active compounds and optionally at least one pharmaceutically acceptable carrier for simultaneous, separate or sequential use.

* * * * *